United States Patent
Liao et al.

(10) Patent No.: US 9,468,695 B2
(45) Date of Patent: Oct. 18, 2016

(54) ULTRAVIOLET LIGHT SOURCE AND METHODS

(71) Applicant: Rayvio Corporation, Hayward, CA (US)

(72) Inventors: Yitao Liao, Hayward, CA (US); Robert C. Walker, Hayward, CA (US)

(73) Assignee: RAYVIO CORPORATION, Hayward, CA (US)

( * ) Notice: Subject to any disclaimer, the term of this patent is extended or adjusted under 35 U.S.C. 154(b) by 0 days.

(21) Appl. No.: 14/645,290

(22) Filed: Mar. 11, 2015

(65) Prior Publication Data
US 2016/0089457 A1    Mar. 31, 2016

(30) Foreign Application Priority Data
Sep. 25, 2014   (CN) .......................... 2014 1 0499470

(51) Int. Cl.
*A61L 2/10*       (2006.01)
*G06F 1/16*       (2006.01)
*H05K 5/02*       (2006.01)

(52) U.S. Cl.
CPC ............... *A61L 2/10* (2013.01); *G06F 1/1613* (2013.01); *H05K 5/0247* (2013.01)

(58) Field of Classification Search
USPC ............... 250/453.11, 454.11, 455.11, 493.1, 250/504 R, 504 H; 422/22, 23, 24
See application file for complete search history.

(56) References Cited

U.S. PATENT DOCUMENTS

2015/0090904 A1* 4/2015 Cole .................... A61L 2/10
                                                                    250/492.1

* cited by examiner

*Primary Examiner* — Nicole Ippolito
(74) *Attorney, Agent, or Firm* — Richard T. Ogawa; Ogawa P.C.

(57) ABSTRACT

A UV device includes a housing having a portion configured to be removably attached to a smart device, a UV light source disposed within the housing, wherein the UV light source is configured to provide output of UV light in response to an operating powered, a communication mechanism disposed within the housing, wherein the communication mechanism is configured to receive instructions from the smart device, a control mechanism disposed within the housing, wherein the control mechanism is coupled to the UV light source, and to the communication mechanism, wherein the control mechanism is configured to provide the operating power to the UV light source, in response to the instructions received from the smart device.

25 Claims, 4 Drawing Sheets

ULTRAVIOLET LIGHT SOURCE AND METHODS

CROSS-REFERENCE TO RELATED APPLICATIONS

The present invention claims the benefit of Chinese Patent Application No. 201410499470.7, filed Sep. 25, 2014, which is incorporated herein by reference in its entirety, for all purposes.

BACKGROUND OF THE INVENTION

The present invention relates to a mobile communications device and methods of operation. More specifically, embodiments of the present invention relate to a mobile communications device, such as a smart phone, including an ultraviolet light source, and methods of controlling the ultraviolet light source using the smart phone.

The inventor of the present invention is aware of the use of ultraviolet light for disinfectant purposes. Currently, there are few stand-alone products on the market that provide ultraviolet light for cleaning surfaces or purifying water. One such product is a hand held UV wand that is plugged into a wall socket, and waved over surfaces; and another such product is a hand-held unit that runs on batteries, and is inserted to sanitize a bottle of water.

Some drawbacks contemplated by the inventor, to such devices include the high power consumption of such devices limit utility of such devices. For example, surface sanitizers are typically bulky and need to be powered by plugging them into a wall socket; and portable water sanitizers use batteries, but drain them quickly. Additional drawbacks are when the user travels, the user must remember to bring along. Because of gadget overload, such dedicated ultraviolet light (UV) sources are not believed to be widely adopted.

It is desired to have an ultraviolet light source without the drawbacks described above.

BRIEF SUMMARY OF THE INVENTION

The present invention relates to a mobile communications device and methods of operation. More specifically, embodiments of the present invention relate to a mobile communications device, such as a smart phone, including an ultraviolet light source, and methods of controlling the ultraviolet light source using the smart phone.

In some embodiments, a case or dongle for a smart phone is contemplated having an integrated ultraviolet (UV) light source and a power source, e.g. batteries. In such embodiments the UV light source may be located near one or more holes of the case, or anywhere else, where the camera of a smart phone is located. In some embodiments, power for the UV light may be drawn from the smart phone or from the case or dongle.

In some embodiments, a smart phone is contemplated having an integrated UV light located near the camera of a smart phone is located, or anywhere else. In some embodiments, power for the UV light may be drawn from the smart phone.

In some embodiments, application software is installed upon the smart phone, and programs the processor of the smart phone to perform one or more operations. Some operations may include monitoring a camera image or accelerometers, directing the UV light to turn on and off, and the like. In some examples, the camera image may be monitored to determine where the UV light is directed towards, may be monitored to determine whether the UV light is pointed upwards or downwards, etc. In other examples, the camera image may be used to determine if the UV light is close enough to a surface for disinfectant purposes, or the like.

In some embodiments, accelerometers, gyroscopes, etc. may also be used to determine orientation of the smart phone. In particular, if the UV light of the smart phone is directed upwards, the power may be shut-off from the UV light; while the UV light of the smart phone is directed, e.g. within 45 degrees of downwards, the UV light may be turned on, or the like.

In various embodiments, using data from one or more of these sensors, the smart phone may be programmed to indicate to the user how long to hold the UV light source of the smart phone over a particular surface; when a particular surface is sanitized and when to move the UV light source of the smart phone to a new location; or the like. In addition, the smart phone may be programmed to turn off the UV light upon unsafe usage conditions.

According to one aspect of the invention, a device for providing ultraviolet light is disclosed. One device includes a shell for a portable device, wherein the shell includes an interior region and an exterior region, wherein the interior region is adapted to be disposed adjacent to the portable device. An apparatus includes a power source configured to provide electrical power, and an ultraviolet light source coupled to the power source and embedded into the exterior region of the shell, wherein the ultraviolet light source is configured to output the ultraviolet light in response to the electrical power.

According to another aspect of the invention, a method for providing ultraviolet light includes providing a shell having an interior region and an exterior region, wherein the shell comprises an ultraviolet light source embedded into the exterior region of the shell, wherein the ultraviolet light source is configured to output ultraviolet light. A technique may include disposing a portable device adjacent to the interior region within the shell, and powering the ultraviolet light source to cause the ultraviolet light source to output the ultraviolet light to a plurality of surfaces. In other aspects, a method includes coupling a UV source dongle to the portable device, e.g. plugging into an interface/power port of the portable device.

Additional objects, features and advantages of the present invention can be more fully appreciated with reference to the detailed description and accompanying drawings that follow.

BRIEF DESCRIPTION OF THE DRAWINGS

In order to more fully understand the present invention, reference is made to the accompanying drawings. They are not to be considered limitations in the scope of the invention, the presently described embodiments and the presently understood best mode of the invention are described with additional detail through use of the accompanying drawings in which.

DETAILED DESCRIPTION OF THE INVENTION

Figure 1:
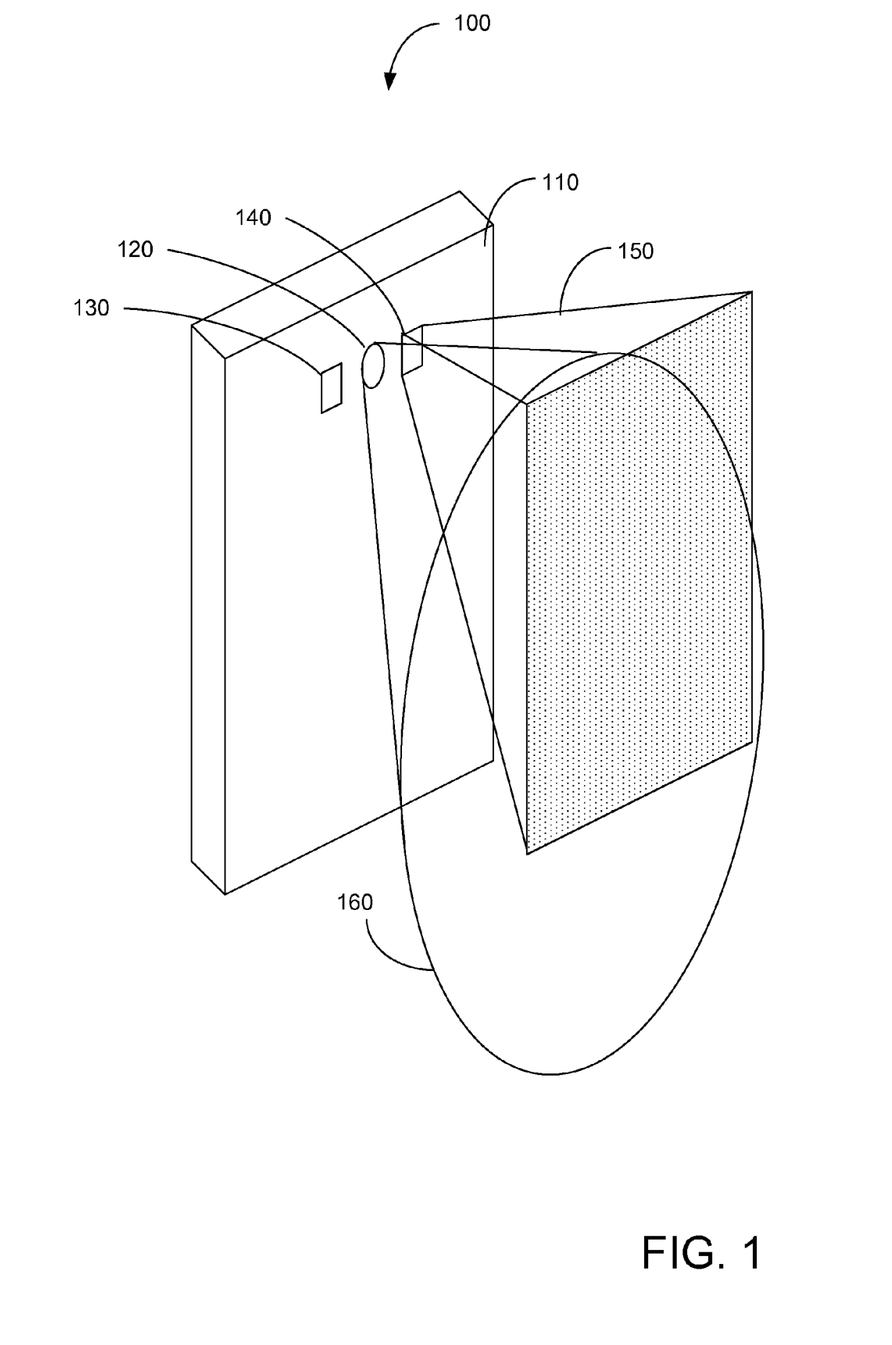
FIG. 1 illustrates an example of various embodiments of the present invention.

FIG. 1 illustrates various embodiments of the present invention. More specifically, FIG. 1 illustrates a hand-held computing device (e.g. smart phone, tablet) 100. In various embodiments, as illustrated, the back casing 110 of device 100, may include a camera 120, a LED light source (e.g. flash) 130, and a UV light source 140. In FIG. 1, UV light source 140 may be positioned such that light 150 from the UV light source 140 is within a field of view 160 of camera 120. In other embodiments, light 150 may not be within field of view 160. UV light source 140 may be positioned on the side, top, bottom, or the like of smart device 100.

Figure 2:
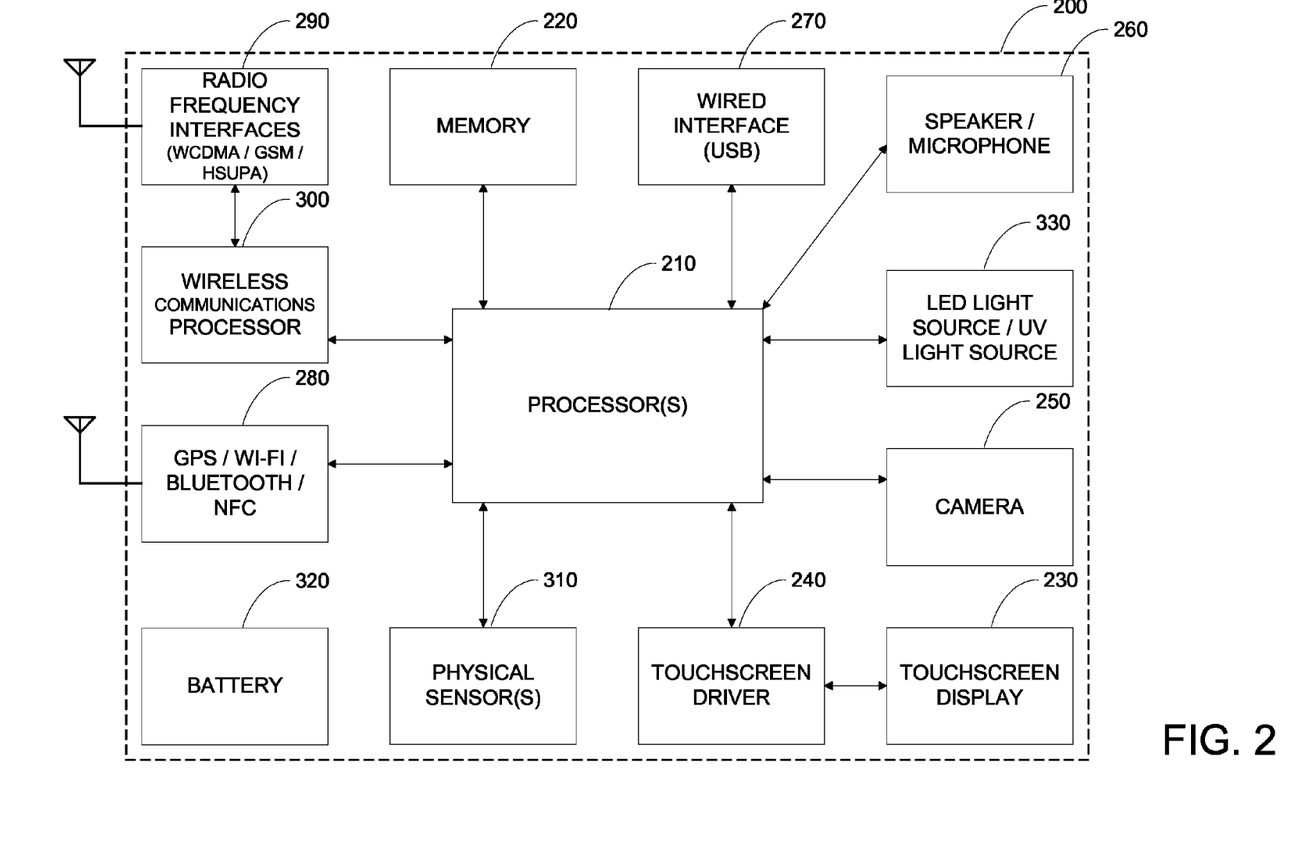
FIG. 2 illustrates a functional block diagram of embodiments of the present invention.

FIG. 2 illustrates a functional block diagram of various embodiments of the present invention (smart device), e.g. iPad, iPhone, Nexus, etc. In FIG. 2, a computing device 200 typically includes an applications processor 210 (e.g. A7 Core, Tegra), memory (including controllers) 220 (e.g. DRAM, Flash), a touch screen display 230 (e.g. OLED, IPS) and driver 240, a camera 250 (e.g. CMOS, CCD), audio input/output devices 260 (speakers/microphone), and the like. Communications from and to computing device are typically provided by via a wired interface 270, a GPS/Wi-Fi/Bluetooth interface 280, RF interfaces 290 (e.g. CDMA, GSM, HSUPA) and processor 300, and the like. Also included in various embodiments are physical sensors 310, e.g. multi-axis Micro-Electro-Mechanical Systems (MEMS) including accelerometers, gyroscopes, magnetometers, pressure sensors, or the like. In various embodiments, operating systems may include iOS, Windows Mobile, Android, or the like.

In some embodiments, computing device may include an integrated UV light source 330. The UV light source 330 may be embodied as a UV light source being developed by the assignee of the present patent application, RayVio, although other sources may also be used. In some embodiments, UV light source 330 may include a UV LED that outputs light within the UV-A range, the UV-B range, and/or the UV-C range.

FIG. 2 is representative of one computing device 200 capable of embodying the present invention. It will be readily apparent to one of ordinary skill in the art that many other hardware and software configurations are suitable for use with the present invention. Embodiments of the present invention may include at least some but need not include all of the functional blocks illustrated in FIG. 2. For example, in some embodiments, the hand-held computing device need not be a multi-purpose smart-device, but may be a dedicated device. Further, it should be understood that multiple functional blocks may be embodied into a single physical package or device, and various functional blocks may be divided and be performed among separate physical packages or devices.

Figure 4A:
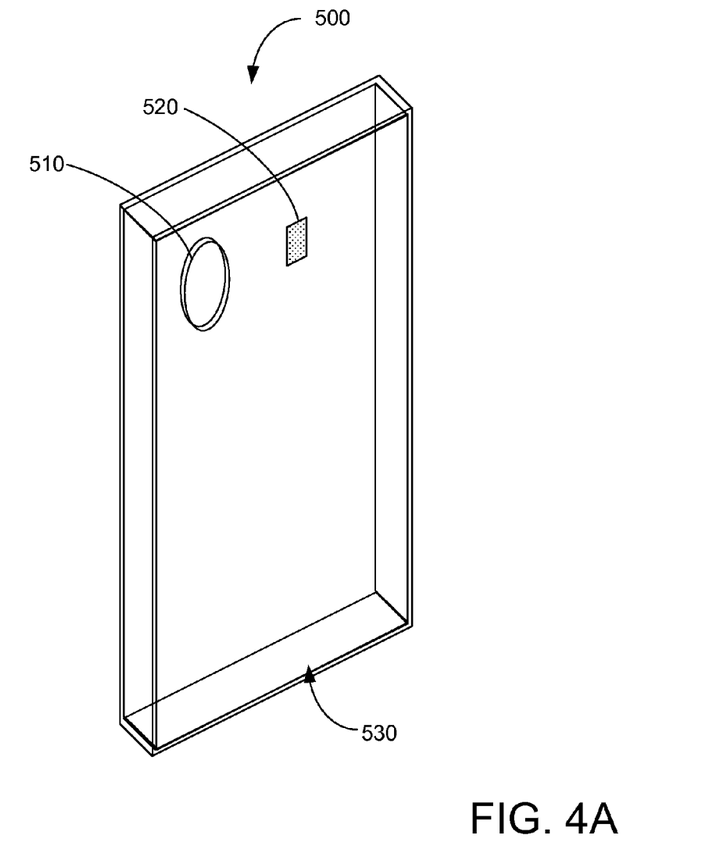
FIGS. 4A-B illustrate examples of various embodiments of the present invention.
Figure 4B:
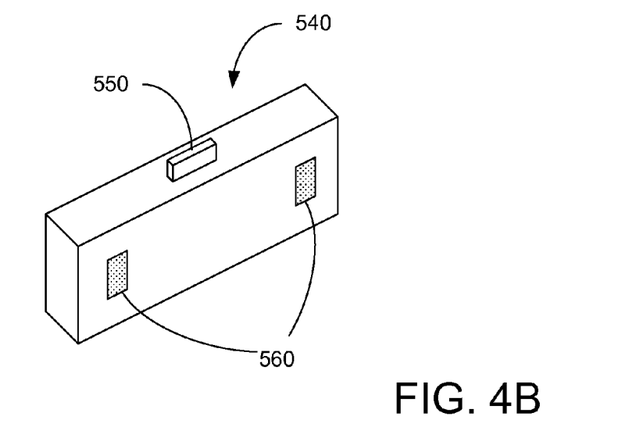

In some embodiments, as illustrated in FIGS. 4A-B, the UV light source may be embodied in a protective case for a smart device (FIG. 4A), and/or a device that can be attached and detached from a smart device (FIG. 4B). As will be discussed below, such devices may include a UV light source, power source, UV controller, physical sensors (MEMS), wired or wireless communications capability, or the like. It should be understood that the processes described herein may be applied to the integrated smart device embodiments discussed in conjunction with FIG. 1, as well as the peripheral embodiments discussed in conjunction with FIGS. 4A and 4B, below.

Figure 3:
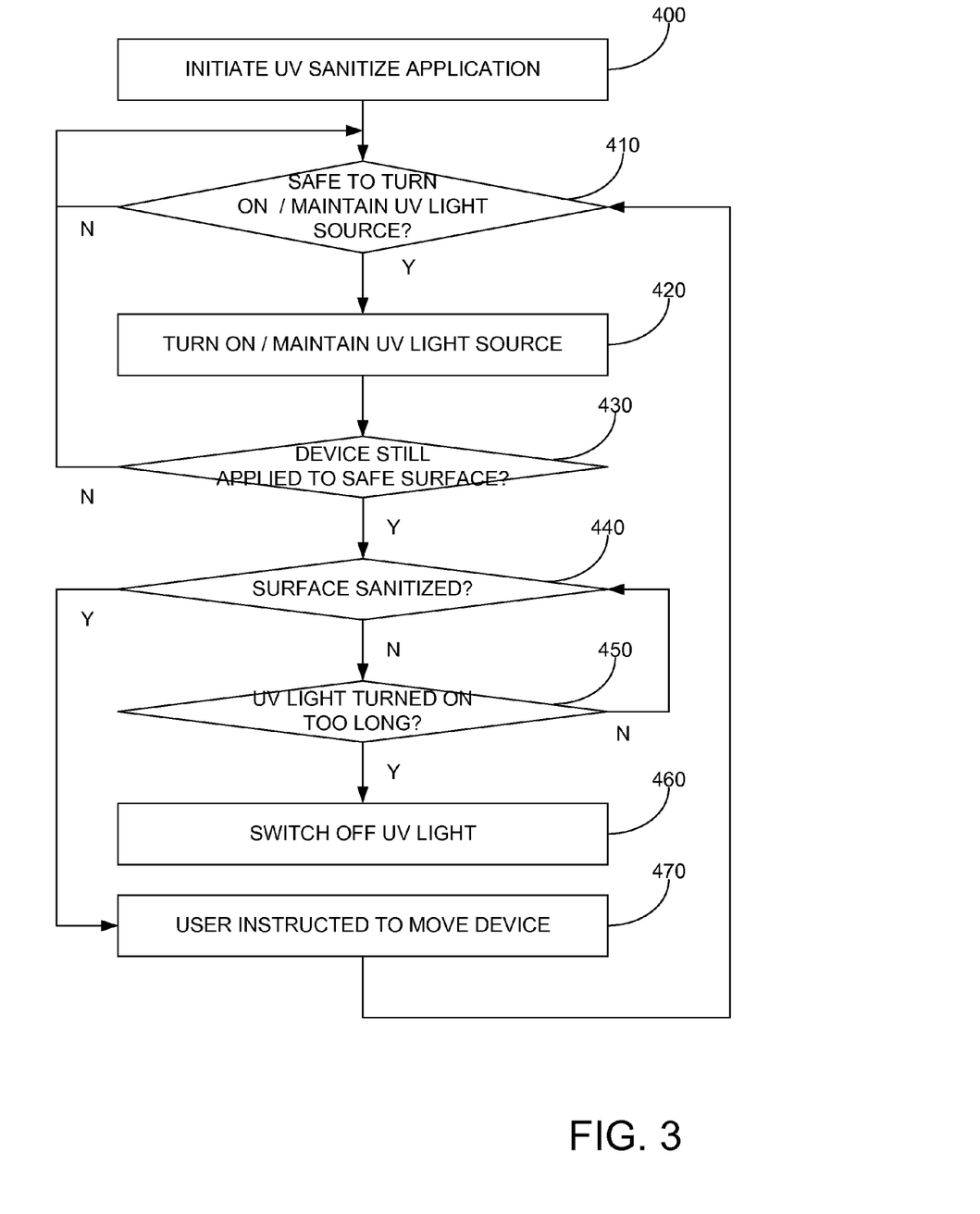
FIG. 3 illustrate block diagrams of flow processes of various embodiments.

FIG. 3 illustrates block diagrams of flow processes according to some embodiments. More specifically, FIG. 3 describes a disinfection or sanitization process. Initially, the user initiates an application (software) upon the smart device to start a UV sanitation process, step 400. This may include the user tapping upon an application icon of a display of the smart device, the user hitting a physical button on the smart device, a software timer going off, or the like.

In some embodiments, the smart device determines whether it is safe to turn on or keep on the UV light, step 410. In some embodiments, this may include the smart device monitoring the MEMS sensors and/or cameras, discussed above, to ensure that the UV light of the smart phone is directed towards a "safe" direction, e.g. the ground, e.g. not upwards towards the face of the user. In some embodiments, this may include the smart device monitoring the amount of light reaching the camera. For example, if there is little light reaching a downwards facing camera, but a lot of light reaching an upwards facing camera, it might be assumed that the UV light faces a surface being sanitized and can be considered safe to be turned on. In another example, if the tilt angle of the downwards orientation is within +/-10 degrees, +/-45 degrees, or the like from downwards, as sensed by the MEMS, the UV light may still be considered safe to be turned on. In some embodiments, based upon the tilt angle, the amount of UV may be varied, for example, at 0 degrees, the UV light may be 100%, at 10 degrees, the UV light may be 50%, etc. In other embodiments, combinations of MEMS sensors and optical detection may be used for this step.

In some embodiments, images from the cameras may be processed by pattern recognition software to provide additional capabilities. In some examples, images from a downwards facing camera (UV assuming the light is also directed downwards) can be used to help determine if the UV light is directed towards a safe surface for sanitization. In some examples, if the downwards facing camera captures an image of a face, animal, skin, or the like, the UV light may be inhibited; if neither the upwards facing camera nor the downwards facing camera recognizes a face, only then can the UV light may be allowed; or the like. In some embodiments, only groups of specific surfaces can be sanitized, after these surfaces are visually identified. As examples, when surfaces with printed letters, e.g. keyboards, magazines, airplane emergency cards are identified by character recognition software, the UV light source may be enabled. In other examples, surfaces to be sanitized may be enabled and/or identified by bar-code, QR code, image, target, or the other such identifier. In such examples, only surfaces bearing such identifiers can be sanitized. One of ordinary skill in the art will recognize many other examples of image recognition that may be used in various embodiments of the present invention.

In some embodiments, a focus distance of the camera may be used to determine whether the UV light source is inhibited or not. For example, in some embodiments, when camera determines that the surface is within about 6 inches away from the camera/UV light source, the UV light may be activated; and for safety sake, when the distance is further than 6 inches, the UV light source may be deactivated. In various embodiments, the safety measures may be implemented as a combination of hardware and software. In some cases, the user may be able to override safety measure in certain circumstances and turn on the UV light, e.g. with a click-through agreement, age verification, password verification, fingerprint recognition, biometric recognition, or the like. In other cases, certain safety measures may not be overridden, e.g. UV light is turned off if the UV light is pointed upwards and a face is detected in the field of view of the camera.

In various embodiments, if safe, power may be applied to the UV light and one or more timers may be initiated, step 420. When the UV light is turned on, the user may be notified, for example, an auxiliary visible light source may turn on, the display of the smart device may turn blue, a sound may be emitted, a vibration may be produced, etc.

In various embodiments, while the UV light is positioned over a particular surface, the cameras and/or the MEMS sensors may be used to determine whether the smart phone has moved, step 430. In some embodiments, to sanitize a surface, the surface should be exposed to UV light for a certain amount of time. However, if the user moves the UV light around, a keyboard, for example, regions of the keyboard may not be sufficiently exposed to the UV light. Accordingly, based upon optical tracking (from camera images), and/or MEMS sensors, the smart device can recognize what surface the UV light is illuminated.

In various embodiments, based upon pattern recognition and/or image stitching functions, software can determine how long different parts of surface, e.g. a keyboard, have been exposed to UV light. In such an example, the application software can determine that the asdf keys were exposed to UV light for 15 seconds, and thus sanitized, but the jkl; keys were exposed to UV light for only 5 seconds, thus further exposure is necessary. In some embodiments, as the user scans across a surface, multiple images of the surface may be captured and stitched together automatically, and as the UV light is swept across the surface, approximate exposure times for different portions of the surface are associated with portions of the stitched image. In various embodiments, movement sensors may provide feedback regarding an optimal scanning rate of the UV light over the surface.

In some embodiments, the timers may be used to determine whether the UV light has exposed a surface a sufficient period of time, step 440, and/or to determine whether the UV light has been powered on for too long, step 450. In the latter case, the UV light may be automatically switched off, step 460. In other embodiments, many other such timers may be used for similar purposes. The amount of time may vary upon the type of surface to be disinfected, for example, fruit, water, and plastic surfaces may require different exposure times.

In various embodiments, after a particular surface has been exposed to UV light for a sufficient period of time, the smart device may notify the user, e.g. sound, image, vibration. In some embodiments, the user may terminate the above process at any time.

FIG. 4A illustrates another embodiment, a protective housing 500 for a smart device.

As illustrated, protective housing 500 may include an opening 510 where the camera of the smart device is positioned. Additionally, housing may include a UV light source 520, typically near opening 510, and a region 530 for a power source, e.g. battery. In other words, in some embodiments, UV light source 520 receives power from a smart device that is nestled within protective housing 500. For example, a plug, or the like may be provided that physically plugs into a port of the smart device and draws power therefrom. In some embodiments, the port may be an I/O port, power port, peripheral port, USB, Firewire or other ports. In such embodiments, the smart device may control light from UV light source 520 by selectively applying power over the port, as was discussed. In particular, under control of one or more software applications running upon the smart device, the UV light may be turned on or off, and the UV light intensity may be adjusted. In some embodiments, housing 500 communicates with smart device via a wireless communication mechanism, e.g. Bluetooth, NFC, or the like, or a wired connection, e.g. a tether.

In other embodiments, protective housing 500 may include an internal battery, e.g. an external battery pack for the smart device, from which to draw power. In such embodiments, the UV light upon housing 500 may still be under the control of the smart device, as discussed above, and/or under the control of housing 500. For example, housing 500 may have a physical enable button or switch for the UV light, and if enabled, the smart device can power on the UV light source. In another example, housing 500 may have a MEMS device that senses when the UV light is pointed upwards, and disables the UV light from being powered-on, even though the smart phone tries to power-on the UV light. In other embodiments, power may be drawn from the smart device via a USB port, Firewire port, headphone port, or the like.

In various embodiments of housing 500, exposure of UV light source 520 may be within a field of view of a smart device camera. In other embodiments, e.g. relying upon MEMS devices, exposure and field of view for the camera may not overlap. MEMS accelerometers, or the like may be integrated into protective housing 500 in some embodiments, for the purposes previously discussed above.

FIG. 4B illustrates another embodiment of the present invention, a dongle (peripheral) or device 540 for a smart device. In this embodiment, dongle 540 typically includes a physical and/or mechanical interface 550 for attachment onto and detachment from a smart device. In various embodiments, device 540 includes one or more UV light sources 560. Dongle 540 may be self-powered (e.g. via battery) or may be powered by the smart device.

In some embodiments, device 540 may be physically attached to a smart device in operation. The UV light sources 560 may operate with and/or be controlled by smart device, similar to the embodiments described above. Additionally, UV light sources 560 may receive power from smart device or an internal battery.

In other embodiments, device 540 may be physically detached from a smart device in operation. Once detached, the user may point UV light sources 560 towards a surface to sanitize, and active UV light sources 560 through software operating upon the smart device. In some embodiments, device 540 may include a proximity sensor, image sensor, or the like. The sensor may be used by device 540 to determine whether the surface is within a distance, e.g. within 6 inches, of UV light sources 560. If so, device 540 may allow the smart device to activate UV light sources. In some embodiments, device 540 may include position sensors, e.g. MEMS accelerometers, or the like. Such position sensors may also be used by device 540 to determine whether UV light sources 560 are pointed downwards. If so, device 540 may allow the smart device to activate UV light sources.

In some embodiments, device 540 may be relatively water-proof. In some examples, device 540 is separated from the smart device and then immersed in water to disinfect or sanitize the water. As described above, device 540 may be partially controlled by smart device during the sanitization process.

In the various embodiments described above, for sanitization or disinfection purposes, the UV LED light sources are typically within the UV-C band, although UV-A band and UV-B band also provides some degree of sanitization. In such embodiments, a blue-colored LED (and/or a UV-A LED) may also be used. Since UV-C is typically not visible to the human eye, the blue-colored LED is a visual indicator for a user that shows whether the UV-C light is active. Additionally, in some embodiments, the blue LED illuminates the same area as the UV-C LED. Accordingly the user will sanitize a surface by directing the blue light towards that surface. The supplemental blue LED may be used in any of the above-described embodiments.

FIG. 6 illustrates block diagrams of flow processes according to some embodiments. More specifically, FIG. 6 describes a UV inspection process. Initially, the user initiates an application (software) upon the smart device to start a UV inspection process, step 600. This may include the user tapping upon an application icon of a display of the smart device, the user hitting a physical button on the smart device, a software timer going off, or the like.

In some embodiments, the smart device determines whether it is safe to turn on or keep on the UV-A light, step 610. Similar to the embodiments described above, the process may include the smart device monitoring the MEMS sensors and/or cameras for unsafe situations. For example, pattern recognition software can be used to ensure the UV-A light is not pointed to a person's face, an animal, or the like; and/or pointed to an appropriate surface, e.g. computer keyboard, printed media, cloth faces, etc. As merely another example, a camera focal distance, a reflected UV light detector, a proximity sensor, or the like may be used to limit the distance between the UV light and the surface.

In various embodiments, if safe, power may be applied to the UV-A wavelength LED and one or more timers may be initiated, step 620. When the UV light is turned on, the user may be notified, for example, an auxiliary visible light source may turn on, the display of the smart device may turn blue, a sound may be emitted, a vibration may be produced, etc.

In various embodiments, in step 630, the safety metrics determined in step 610 are monitored. While still safe, in some embodiments, a software application running on the smart device may allow the user to capture a photograph of the surface, step 640. In some embodiments, no visible-light flash is used when capturing the image, so that the natural fluorescence of the surface in response to the UV-A light is captured, step 670. In some examples, driver's licenses, passports, currency, quality labels, and the like may include UV-A responsive ink as a fluorescence source. Accordingly, in this step, an image of the fluorescence can be used for bookkeeping, evidentiary purposes, or the like. As merely an example, the image may show the fluorescence of bed-bugs on a bed, the fluorescence of pathogens on a surface, or the like.

In some embodiments, a visible-light flash may be used during image capture. For example, it is contemplated that the UV-A light source may be used by a user to physically inspect a surface, e.g. passport, for authentication purposes. Subsequently, when the user wants to take a picture of the surface, the flash is activated so a visible light image of the surface may be captured, step 670. Again, the visible light image may be used for bookkeeping, evidentiary purposes, or the like. As merely an example, the image may be a driver's license of a person going through airport security.

Next, in various embodiments, a determination is made whether the UV light has been powered on for too long, step 650. In the latter case, the UV light may be automatically switched off, step 660. In other embodiments, many other such timers may be used for similar purposes. The amount of time may vary upon the intensity of the UV light, the temperature, and the like.

Further embodiments can be envisioned to one of ordinary skill in the art after reading this disclosure. For example, in some embodiments, a UV light sensor may be included on the smart device, protective case, dongle, or the like. The UV light sensor may be positioned proximate to the one or more UV light sources. In operation, the UV sensor may be used to determine if UV light is reflected from a surface, and/or an intensity of reflected UV light. In one embodiment, when reflected UV light is not detected, the UV light source may not be pointed at a surface, for example, the UV light source may be pointed into space. In such an embodiment, the amount of UV light output from the UV light sources may be decreased or pulsed for safety's sake. When reflected UV light is subsequently detected by a UV light sensor, it may be assumed that UV light is reflecting off of a relatively close surface. Accordingly, the UV light source output may be increased to the desired UV light intensity. In some embodiments, if too much reflected UV light is detected, the UV light intensity may be decreased.

In other embodiments, combinations or sub-combinations of the above disclosed invention can be advantageously made. For example, in some embodiments, the UV light peripheral may be stored separate from the smart device. In operation, the user would plug-in the UV peripheral into the smart device, and the UV peripheral would draw power and/or receive instructions from the smart device. Software applications running on the smart device would then selectively activate and deactivate the UV light source on the UV peripheral. When disinfecting, the user would then move their smart device (and the attached UV light source) over the treatment surface. After satisfactory completion, the user may detach the UV light peripheral from the smart device, and physically store the peripheral separate from the smart device. In other embodiments, the UV light peripheral may be stored adjacent to the smart device. The block diagrams of the architecture and flow charts are grouped for ease of understanding. However it should be understood that combinations of blocks, additions of new blocks, re-arrangement of blocks, and the like are contemplated in alternative embodiments of the present invention.

The specification and drawings are, accordingly, to be regarded in an illustrative rather than a restrictive sense. It will, however, be evident that various modifications and changes may be made thereunto without departing from the broader spirit and scope of the invention as set forth in the claims.

We claim:

1. A portable UV device comprising:
   a housing having a portion configured to be removably attached to a portable smart device by a user;
   a UV light source disposed within the housing, wherein the UV light source is configured to provide output of sanitizing UV light and configured to sanitize a plurality of target surfaces other than a surface of the portable smart device in response to an operating powered provided thereto;
   a communication mechanism disposed within the housing, wherein the communication mechanism is configured to receive instructions from the smart device; and
   a control mechanism disposed within the housing, wherein the control mechanism is coupled to the UV light source, and to the communication mechanism, wherein the control mechanism is configured to provide the operating power to the UV light source, in response to the instructions received from the smart device; and wherein the portable UV device is configured to be physically moved independently from the portable smart device over the plurality of target surfaces by the user to provide the sanitizing UV light to the plurality of target surfaces other than the surface of the portable smart device.

2. The UV device of claim 1 wherein the communication mechanism is selected from a group consisting of: NFC, Bluetooth, Wi-Fi, RF, IR, a tethered connection.

3. The UV device of claim 1 wherein the communication mechanism configured to send data to the smart device, wherein the data is selected from a group consisting of: a status of the UV light source, a status of the power source, positional data of the UV device, proximity data of the UV light source to a surface.

4. The UV device of claim 1 wherein the UV device further comprises a proximity sensor disposed within the housing, wherein the proximity sensor determines a proximity of the UV light source to a surface.

5. The UV device of claim 4 wherein the proximity sensor is selected from a group consisting of: an image sensor, a UV light sensor, a visible light sensor, a camera sensor, and a sonic sensor.

6. The UV device of claim 1 wherein the portion of the housing comprises a male connector selected from a group consisting of: micro USB and Apple Lightning.

7. The UV device of claim 6 wherein the control mechanism receives the operating power from the smart device via the male connector.

8. The UV device of claim 1 further comprising a female connector disposed within the housing, wherein the female connector selected from a group consisting of: micro USB and Apple Lightning.

9. The UV device of claim 1 further comprising a power source disposed within the housing, wherein the power source is configured to provide the operating power.

10. The UV device of claim 1 wherein the UV light source is selected from a group consisting of: UV-A LED, UV-B LED, UV-C LED.

11. A UV illumination method comprising:
retrieving a smart device having physically coupled thereto a UV peripheral in a proximate storage position;
selecting by a user, an UV illumination application for execution upon the smart device;
physically decoupling by the user, the UV peripheral from the proximate storage position on the smart device;
while the UV peripheral is physically decoupled from the proximate storage position, the method further comprises:
 selecting by the user, an icon from within the UV illumination application executing upon the smart device, wherein the UV peripheral outputs UV light in response to the selection of the icon; and
 physically moving by the user, the UV peripheral above a plurality of target surfaces to thereby expose the plurality of target surfaces to UV light; and thereafter
physically recoupling by the user, the UV peripheral to the proximate storage position on the smart device.

12. The UV illumination method of claim 11 wherein while the UV peripheral is physically decoupled from the proximate storage position, the method further comprising:
depressing and holding down by the user, of a button on the UV peripheral; and
wherein the UV peripheral outputs UV light in response to the selection of the icon and the holding down of the button on the UV peripheral.

13. The UV illumination method of claim 12 wherein the UV peripheral is inhibited from outputting UV light when the button is not held down.

14. The UV illumination method of claim 11 wherein moving the peripheral above the plurality of target surfaces is in response to visual instructions displayed by the UV illumination application on the smart device to the user.

15. The UV illumination method of claim 14 wherein the visual instructions displayed by the UV illumination application on the smart device include instructions to the user to move the UV peripheral slower or faster.

16. The UV illumination method of claim 11 wherein the UV peripheral is inhibited from outputting UV light in response to certain conditions monitored by the smart device.

17. The UV illumination method of claim 16 wherein the conditions monitored by the smart device are selected from a group consisting of: proximity of the UV peripheral to the plurality of target surfaces, a class of prohibited target surfaces, direction of illumination of the UV light, remaining power stored in the UV peripheral, and illumination duration.

18. The UV illumination method of claim 11 further comprising:
physically coupling a power-input cable to the UV peripheral, wherein power provided by the power-input cable is provided to the smart device and to the UV peripheral.

19. The UV illumination method of claim 11 wherein wavelengths for the UV light is selected from a group consisting of: UV-A, UV-B, UV-C.

20. A UV illumination method comprising:
retrieving a smart device having a peripheral interface;
physically coupling by a user, a UV peripheral to the smart device via the peripheral interface;
selecting by the user, an UV illumination application for execution upon the smart device;
selecting by the user, an icon from within the UV illumination application executing upon the smart device, wherein the UV peripheral outputs UV light in response to the selection of the icon; and
physically moving by the user, the UV peripheral above a plurality of target surfaces while the UV peripheral outputs UV light to thereby expose the plurality of target surfaces to UV light.

21. The method of claim 20 wherein the selecting the icon further comprises providing operating power from the smart device to the UV peripheral via the peripheral interface.

22. The method of claim 20 further comprising physically decoupling by the user, the UV peripheral from the smart device.

23. The method of claim 20 wherein the selecting the icon further comprises:
determining a safe condition indicating whether it is safe to output UV light; and
outputting UV light from the UV peripheral in response to the safe condition.

24. The method of claim 23 wherein the selecting the icon further comprises:
receiving a user safety override instruction from the smart device in response to a lack of the safe condition; and
outputting UV light from the UV peripheral in response to the user safety override instruction.

25. The method of claim 24 wherein the user safety override instruction is determined by the smart device in response to user input on the smart device selected from a group consisting of: user biometric data, user age verification data, user password, and user checkbox.

\* \* \* \* \*